United States Patent [19]
Duerr

[11] 3,975,418
[45] *Aug. 17, 1976

[54] 4-BROMO-3-CHLORO-PHENYLISOCYANATE

[75] Inventor: Dieter Duerr, Bottmingen, Switzerland

[73] Assignee: Ciba-Geigy AG, Basel, Switzerland

[ * ] Notice: The portion of the term of this patent subsequent to July 31, 1990, has been disclaimed.

[22] Filed: May 27, 1975

[21] Appl. No.: 581,253

Related U.S. Application Data

[60] Continuation of Ser. No. 384,348, July 31, 1973, abandoned, which is a division of Ser. No. 63,288, Aug. 12, 1970, Pat. No. 3,749,746, which is a continuation-in-part of Ser. No. 642,140, May 29, 1967, abandoned.

[30] Foreign Application Priority Data

June 22, 1966 Switzerland.......................... 9057/66

[52] U.S. Cl. .......................... 260/453 AR; 71/120; 260/553 A
[51] Int. Cl.² ...................... C07C 119/048
[58] Field of Search .............................. 260/453 AR

[56] References Cited
UNITED STATES PATENTS

| | | | |
|---|---|---|---|
| 3,024,269 | 3/1962 | Barthel, Jr. et al. ............ | 260/453 X |
| 3,429,911 | 2/1969 | Kirchner et al. .................... | 260/465 |
| 3,431,289 | 3/1969 | Freund et al. ...................... | 260/453 |

Primary Examiner—Lewis Gotts
Assistant Examiner—Dolph H. Torrence
Attorney, Agent, or Firm—Frederick H. Rabin

[57] ABSTRACT

The present invention relates to new isocyanates of the formula

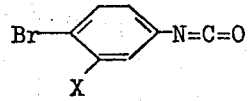

wherein X represents fluorine or chlorine; these new isocyanates of formula I are valuable intermediates for the manufacture of herbicides.

1 Claim, No Drawings

4-BROMO-3-CHLORO-PHENYLISOCYANATE

CROSS REFERENCE

This is a continuation of application Ser No. 384,348 filed on July 31, 1973, now abandoned, which is a division of application Ser. No. 63,288 filed on Aug. 12, 1970, now U.S. Pat. No. 3,749,746. Application Ser. No. 63,288 is a continuation-in-part of application Ser. No. 642,140 filed on May 29, 1967, now abandoned.

BACKGROUND OF THE INVENTION

The present invention is concerned with isocyanates of the formula

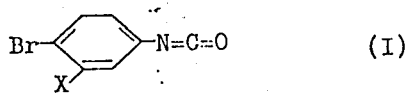

wherein X represents fluorine or chlorine and a process for their manufacture.

The new isocyanates of formula (I) may be manufactured by methods which are in themselves known.

In principle, two general methods are available:

A. An isocyanate of the formula

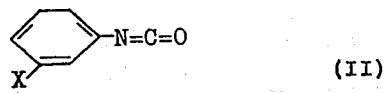

can be reacted with a brominating agent, or (B) an isocyanate group can be produced in a compound of formula

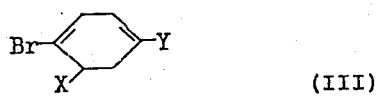

wherein X represents a fluorine or chlorine atom and Y is a nitrogen-containing group that can be converted into an isocyanate group.

If route (A) is to be followed, the bromination is preferably carried out in a solvent or diluent. As the solvent or diluent there may, for example, be used aliphatic or aromatic hydrocarbons.

Of the aliphatic hydrocarbons the halogenated hydrocarbons for example ethylene dichloride or dichlorethylene, dichlorethane, tetrachlorethylene, tetrachlorethane, chloroform and carbon tetrachloride have proved to be especially suitable. Of the aromatic hydrocarbons those which are not susceptible to bromination, or are susceptible to bromination only with difficulty, are preferred, for example perhalogenated benzenes or naphthalenes and nitrobenzene.

As brominating agents there may be used, for example, bromine itself, complexes of bromine, for example pyridine hydrobromide dibromide, aluminium bromide/bromine complexes, and organic compounds which easily release bromine, for example N-bromosuccinimide or N-bromophthalimide. Bromination with molecular bromine at a temperature within the range of from −20°C to 150°C, is the most simple process. Halogenation catalysts, for example, iodine or iron accelerate the reaction. The rate of reaction may be increased by the presence in the reaction mixture of a dimerised or trimerised isocyanate or urea or a symmetrical urea.

If route (B) is to be followed, then the so-called "synthetic reaction" can be used, such as for example the phosgenation of 3-chloro-4-bromaniline or 3-fluoro-4-bromaniline or of its hydrochloride. The phosgenation is preferably carried out in a solvent or diluent, for example in toluene, xylene, cumene, chlorobenzene, dichlorobenzene or trichlorobenzene. As a rule elevated temperatures are used, for example those within the range of from 110°C to 200°C. It is of course also possible to phosgenate in the gas phase, in which case the free amine is used in the vapour state.

The isocyanates in question can also be obtained from the corresponding N-halogenamides by the Hofmann reaction or from the corresponding acid azides by the Curtius reaction.

The isocyanates can also be obtained by so-called "reverse decomposition" reactions. Thus, for example, the corresponding isocyanates may be obtained from ureas, for example, the symmetrical ureas, by the action of phosgene.

It is also possible to manufacture the isocyanates by reacting the corresponding phenyldiazonium salts with alkali cyanides in the presence of copper powder.

The desired isocyanates may also be manufactured by means of the Lossen rearrangement of appropriately substituted hydroxamic acids. The usual reagents such as acid anhydrides, preferably, acetic anhydride, phosgene or thionyl chloride may be used as reagents for eliminating water.

The new isocyanates of formula I are above all valuable intermediates for the manufacture of herbicidally active ureas. Especially valuable selective herbicides are obtained when the isocyanates of formula I are reacted according to a known method with a N,N-di-lower alkyl amine. The lower alkyl radicals of the amines contain 1 to 4 carbon atoms each and are preferably methyl groups. Hence, specific compounds are inter alia, N-(3-fluoro-4-bromophenyl)-N',N'-dimethyl urea and N-(3-chloro-4-bromo-phenyl)-N',N'-dimethyl urea; they are prepared by reacting the relevant isocyanate with dimethylamine. Such ureas show an outstanding selective herbicidal activity in cereals, maize, rice, corn, tomatoes, potatoes, soya, cotton, carrots and others. Further possible applications of the compound of formula I are in the textile finishing field.

EXAMPLE 1

4-Bromo-3-chloro-phenylisocyanate 76,7 g of m-chlorophenylisocyanate in 150 ml of dry ethylene chloride was stirred with 80 g of dry bromine in a 500 ml stirred flask having a condenser surmounted by a calcium chloride tube, and a gas outlet, stirrer and thermometer. The temperature was kept at 40°C by cooling with water. A thick suspension resulted. After 2 hours the mixture was heated to reflux until a clear solution was produced and the solvent was then distilled off. The residue which remained was fractionated in vacuo. 73 g of a product of boiling point 122°C to 123°C/12 mm Hg were obtained in the form of crystallised needles, together with 20.5 g of a liquid first run which boiled at 82°C to 122°C/12 mm Hg and predominantly consisted of unchanged m-chlorophenylisocyanate.

EXAMPLE 2

3-Fluoro-4-bromophenylisocyanate was manufactured in a similar manner to that described in Example 1. It boiled at 101°C at 12 mm Hg.

EXAMPLE 3

600 g of 3-chlor-4-bromaniline hydrochloride were suspended in 2500 ml chlorobenzene and the entire mixture was heated to 150°C to 160°C with vigorous stirring. About 1.25 kg of phosgene was introduced at this temperature; after about 10 to 16 hours all the hydrochloride had disappeared. The solvent was distilled off and the residue was rectified in vacuo. In this way 650 g of 3-chloro-4-bromo-phenylisocyanate, boiling at 122°C to 123°C at 12 mm Hg, were obtained.

EXAMPLE 4

1750 g of bis-3-chloro-4-bromophenyl-urea was suspended in 4000 g of chloronaphthalene and the entire mixture was heated to 150°C with vigorous stirring. 800 g of phosgene was then introduced at this temperature over the course of 4 to 5 hours. Thereafter dry air was blown through the charge in order to remove the hydrogen chloride which had formed and the mixture was then worked-up in the usual manner. In this way about 1600 g of pure 3-chloro-4-bromophenylisocyanate were obtained.

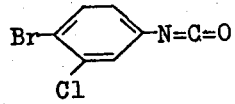

I claim:
1. The isocyanate of the formula